(12) United States Patent
Thiruvenkadam et al.

(10) Patent No.: US 11,017,269 B2
(45) Date of Patent: May 25, 2021

(54) SYSTEM AND METHOD FOR OPTIMIZATION OF DEEP LEARNING ARCHITECTURE

(71) Applicant: General Electric Company, Niskayuna, NY (US)

(72) Inventors: Sheshadri Thiruvenkadam, Bangalore (IN); Sohan Rashmi Ranjan, Bangalore (IN); Vivek Prabhakar Vaidya, Banaglore (IN); Hariharan Ravishankar, Banaglore (IN); Rahul Venkataramani, Bangalore (IN); Prasad Sudhakar, Bangalore (IN)

(73) Assignee: General Electric Company, Schenectady, NY (US)

( * ) Notice: Subject to any disclaimer, the term of this patent is extended or adjusted under 35 U.S.C. 154(b) by 37 days.

(21) Appl. No.: 16/334,091

(22) PCT Filed: Jun. 21, 2017

(86) PCT No.: PCT/US2017/038504
§ 371 (c)(1),
(2) Date: Mar. 18, 2019

(87) PCT Pub. No.: WO2018/063460
PCT Pub. Date: Apr. 5, 2018

(65) Prior Publication Data
US 2019/0266448 A1    Aug. 29, 2019

(30) Foreign Application Priority Data

Sep. 30, 2016   (IN) .............................. 201641033618

(51) Int. Cl.
*G06K 9/62*    (2006.01)
*G16H 30/40*   (2018.01)
(Continued)

(52) U.S. Cl.
CPC ............. *G06K 9/6262* (2013.01); *G06K 9/46* (2013.01); *G06K 9/4628* (2013.01);
(Continued)

(58) Field of Classification Search
CPC .. G06K 9/6262; G06K 9/6271; G06K 9/4628; G06K 9/46; G06K 9/6256;
(Continued)

(56) References Cited

U.S. PATENT DOCUMENTS

| 5,776,063 | A  | * | 7/1998 | Dittrich | ................. | A61B 8/481 |
|           |    |   |        |          |                   | 600/408    |
| 9,401,020 | B1 | * | 7/2016 | Li       | ......................... | G06K 9/481 |

(Continued)

OTHER PUBLICATIONS

International Search Report and Written Opinion for corresponding PCT Application No. PCT/US2017/038504 dated Sep. 11, 2017; 16 pages.

(Continued)

*Primary Examiner* — Xuemei G Chen

(57) ABSTRACT

A method for determining optimized deep learning architecture includes receiving a plurality of training images and a plurality of real time images corresponding to a subject. The method further includes receiving, by a medical practitioner, a plurality of learning parameters comprising a plurality of filter classes and a plurality of architecture parameters. The method also includes determining a deep learning model based on the plurality of learning parameters and the plurality of training images, wherein the deep learning model comprises a plurality of reusable filters. The method further includes determining a health condition of the subject based on the plurality of real time images and the deep learning model. The method also includes providing the health condition of the subject to the medical practitioner.

20 Claims, 5 Drawing Sheets

(51) Int. Cl.
| | |
|---|---|
| *G06K 9/46* | (2006.01) |
| *G06N 3/08* | (2006.01) |
| *G06N 3/04* | (2006.01) |
| *G16H 50/20* | (2018.01) |
| *G16H 40/63* | (2018.01) |
| *G16H 50/70* | (2018.01) |

(52) U.S. Cl.
CPC ......... *G06K 9/6256* (2013.01); *G06K 9/6271* (2013.01); *G06N 3/0454* (2013.01); *G06N 3/08* (2013.01); *G16H 30/40* (2018.01); *G16H 40/63* (2018.01); *G16H 50/20* (2018.01); *G16H 50/70* (2018.01); *G06K 2209/05* (2013.01)

(58) Field of Classification Search
CPC .... G06K 2209/05; G06N 3/0454; G06N 3/08; G16H 50/20; G16H 40/63; G16H 50/70; G16H 30/40
See application file for complete search history.

(56) References Cited

U.S. PATENT DOCUMENTS

| | | | | |
|---|---|---|---|---|
| 9,524,450 | B2 * | 12/2016 | Ravindran | G06K 9/6292 |
| 9,760,978 | B1 * | 9/2017 | Lu | G06T 5/50 |
| 9,767,410 | B1 * | 9/2017 | Guevara | G10L 15/16 |
| 10,037,457 | B2 * | 7/2018 | Tang | G06K 9/00288 |
| 10,552,705 | B2 * | 2/2020 | He | G06K 9/00536 |
| 2013/0346082 | A1 * | 12/2013 | Aly | G06F 16/90 704/270 |
| 2016/0174902 | A1 | 6/2016 | Georgescu et al. | |
| 2016/0259994 | A1 * | 9/2016 | Ravindran | G06N 3/08 |
| 2016/0321523 | A1 * | 11/2016 | Sen | G06N 7/005 |
| 2017/0076474 | A1 * | 3/2017 | Fu | G06K 9/00268 |
| 2017/0083796 | A1 * | 3/2017 | Kim | G06K 9/00369 |
| 2017/0220891 | A1 * | 8/2017 | Kim | G06N 3/082 |
| 2017/0344900 | A1 * | 11/2017 | Alzahrani | G06N 20/00 |
| 2018/0014130 | A1 * | 1/2018 | Lunner | A61B 5/0476 |
| 2018/0060648 | A1 * | 3/2018 | Yoo | G06K 9/00268 |
| 2018/0182129 | A1 * | 6/2018 | Xing | G06T 11/005 |
| 2019/0147220 | A1 * | 5/2019 | Mccormac | G06K 9/6277 382/103 |
| 2019/0251374 | A1 * | 8/2019 | Sakai | B60R 21/00 |

OTHER PUBLICATIONS

Sironi Amos et al: "Learning Separable Filters", IEEE Transactions on Pattern Analysis and Machine Intelligence, IEEE Computer Society, USA, vol. 37, No. 1, Jan. 1, 2015; pp. 94-106.

Ravishankar Hariharan et al: "Understanding the Mechanisms of Deep Transfer Learning for Medical Images", Sep. 27, 2016, Network and Parallel Computing; pp. 188-196.

Rahul Venkataramani et al: "Filter Sharing: Efficient Learning of Parameters for Volumetric Convolutions", ARXIV.org; Cornell University Library, Ithaca, NY; Dec. 8, 2016; 6 pages.

Hessam Bagherinezhad et al: "LCNN: Lookup-Based Convolutional Neural Network", ARXIV.org; Cornell University Library, Ithaca, NY; Nov. 20, 2016; 10 pages.

\* cited by examiner

|  | Optimized CNN | Conventional CNN |
|---|---|---|
| Without sharing | 93.39% (5250 parameters) | 85.55% (180000 parameters) |
| With sharing | 94.13% (4575 parameters) | 86% (109500 parameters) |

SYSTEM AND METHOD FOR OPTIMIZATION OF DEEP LEARNING ARCHITECTURE

This application is a filing under 35 U.S.C. 371 of international application number PCT/US2017/038504, filed Jun. 21, 2017, which claims priority to India application number 201641033618, filed Sep. 30, 2016, the entire disclosure of each of which is hereby incorporated by reference.

BACKGROUND

Embodiments of the present specification relate generally to a system and method for optimization of deep learning architecture. Specifically, the system and the method are directed towards determining an optimized deep learning architecture using a small set of training data.

Data object classification systems employ rule based classification schemes to classify data objects into one or more pre-determined categories. For example, visual recognition systems can identify objects in images, i.e., classify input images as including objects from one or more object categories. Machine learning models such as neural networks are employed to generate an output such as index of an object category for a received input such as an image to be analyzed. Often, data object classification systems are difficult and expensive to maintain, and insufficient for tasks involving large, varying, or complex data sets. While manual design of such systems is difficult due to high complexity, automatic identification of features may not generate effective data object classification models.

Complex artificial intelligence (AI) tasks, such as scene or language understanding, requiring large quantity of labelled data employ deep learning architectures. A typical example is a multi-layer feed-forward network where the first layers will typically learn levels of feature extraction or processing that are useful to all tasks. In convolution neural networks (CNNs), enough of filters and layers have to be employed) for effective modeling of the underlying non-linearity in the classification task. The estimation of filters and other deep learning parameters requires sufficient amount of training data. In semi-supervised learning, improving the quality of learning networks using unlabeled data employs techniques such as embedding data into a lower dimensional space and clustering of data. Many of these architectures use unsupervised and supervised training techniques in a stage wise manner. Further, the supervised classifier has less number of layers.

In text document analysis, abstract semantics are converted into feature vectors using embedding functions in a deep learning architecture. In determining such architectures, training of deep learning networks employs regularization technique. Further, deep learning architectures are initialized with parameters from previously trained tasks. In multi-task learning, learning models are shared between different classification tasks. However, determining deep learning networks for a given complex learning task is not effective when the training data set is small in size.

BRIEF DESCRIPTION

In accordance with one aspect of the present specification, a method for determining optimized deep learning architecture is disclosed. The method includes receiving a plurality of training images and a plurality of real time images corresponding to a subject. The method further includes receiving, by a medical practitioner, a plurality of learning parameters comprising a plurality of filter classes and a plurality of architecture parameters. The method also includes determining a deep learning model based on the plurality of learning parameters and the plurality of training images, wherein the deep learning model comprises a plurality of reusable filters. The method further includes determining a health condition of the subject based on the plurality of real time images and the deep learning model. The method also includes providing the health condition of the subject to the medical practitioner.

In accordance with another aspect of the present specification, an optimized deep learning sub-system for determining optimized deep learning architecture is disclosed. The system includes an image acquisition unit communicatively coupled to an imaging modality and configured to receive a plurality of training images and a plurality of real time images corresponding to a subject. The system further includes an user interface unit configured to receive, by a medical practitioner, a plurality of learning parameters comprising a plurality of filter classes and a plurality of architecture parameters. The method also includes a model generator unit communicatively coupled to the image acquisition unit and the user interface unit and configured to receive the plurality of training images from the image acquisition unit and the plurality of learning parameters. The model generator is further configured to determine a deep learning model based on the plurality of learning parameters and the plurality of training images, wherein the deep learning model comprises a plurality of reusable filters. The system also includes a processor unit communicatively coupled to the image acquisition unit and the model generator unit and configured to receive a plurality of real time images from the image acquisition unit and the deep learning model from the model generator unit. The processor unit is further configured to determine a health condition of the subject based on the plurality of real time images using the deep learning model. The processor unit is also configured to provide the health condition of the subject to the medical practitioner.

In accordance with another aspect of the present specification, a health diagnostic system is disclosed. The health diagnostic system includes an imaging modality and an optimized deep learning sub-system. The optimized deep learning sub-system includes an image acquisition unit communicatively coupled to the imaging modality and configured to receive a plurality of training images and a plurality of real time images corresponding to a subject. The optimized deep learning sub-system includes an user interface unit configured to receive, by a medical practitioner, a plurality of learning parameters comprising a plurality of filter classes and a plurality of architecture parameters. The optimized deep learning sub-system also includes a model generator unit communicatively coupled to the image acquisition unit and the user interface unit and configured to receive the plurality of training images from the image acquisition unit and the plurality of learning parameter. The model generator is further configured to determine a deep learning model based on the plurality of learning parameters and the plurality of training images, wherein the deep learning model comprises a plurality of reusable filters. The optimized deep learning sub-system further includes a processor unit communicatively coupled to the image acquisition unit and the model generator unit and configured to receive a plurality of real time images from the image acquisition unit and the deep learning model from the model generator unit. The processor unit is further configured to determine a health condition of the subject based on the plurality of real time images using the deep learning model. The processor unit is also configured to provide the health condition of the subject to the medical practitioner.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of systems and methods for determining optimized deep learning architecture are presented. In particular, use of the systems and methods presented hereinafter allows optimizing the convolution neural network based on reusable filters.

The term 'deep learning' refers to machine learning technique having capability of determining features. The term 'deep learning architecture' refers to structures used by the deep learning techniques. The term 'deep learning structure' is used herein equivalently and interchangeably with the term 'deep learning model'. The term 'learning parameters' used herein refers to parameters and initial conditions required to generate the deep learning model.

Figure 1:
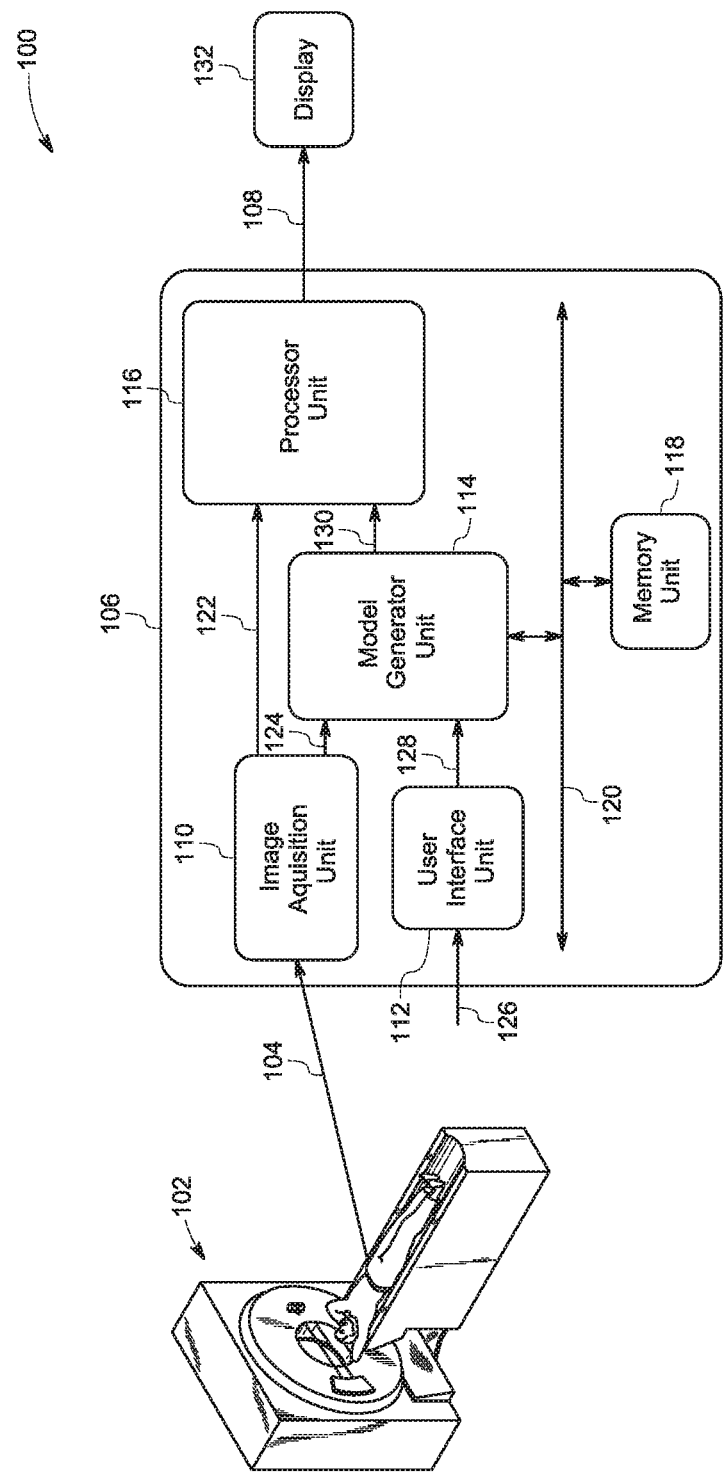
FIG. 1 is a block diagram representation of a health diagnostic system using an optimized deep learning architecture, in accordance with aspects of the present specification.

FIG. 1 is a block diagram representation of a health diagnostic system 100 using a deep learning architecture, in accordance with aspects of the present specification. The health diagnostic system 100 includes an imaging modality 102, such as a magnetic resonance imaging (MRI) system configured to generate a plurality of images, generally represented by reference numeral 104, corresponding to a subject (not shown in FIG. 1). In other embodiments, the imaging modality 102 may be any other imaging system such as, but not limited to, a computer tomography (CT) system and a positron emission tomography (PET) system. The health diagnostic system 100 further includes an optimized deep learning sub-system 106 communicatively coupled to the imaging modality 102 and configured to generate a diagnostic information representative of a health condition, generally represented by reference numeral 108, corresponding to the subject.

In the illustrated embodiment, the optimized deep learning sub-system 106 includes an image acquisition unit 110, a user interface unit 112, a model generator unit 114, a processor unit 116, and a memory unit 118 communicatively coupled to one another. In the illustrated embodiments, the various units of the optimized deep learning sub-system 106 are coupled to one another through a communication bus 120.

The image acquisition unit 110 is communicatively coupled to the imaging modality 102 and configured to receive a plurality of images 104 corresponding to the subject. The plurality of images 104 includes a plurality of training images 124 and a plurality of real time images 122. In one embodiment, the plurality of training images 124 correspond to a plurality of images acquired in the past and stored in a memory associated with the imaging modality 102. The plurality of training images 124 may also include additional data such as, but not limited to, one or more features of the images, a health condition of the subject, and a diagnostic information. In certain embodiments, the training images 124 may be used to determine a deep learning model usable in determining a diagnostic information based on the real time images 122.

The image acquisition unit 110 is further configured to perform one or more data conditioning operations on the plurality of images 104. Non-limiting examples of such data conditioning operations may include noise reduction, frame rate change, and modification of a size of the images 104.

The user interface unit 112 is configured to receive external inputs, represented by reference numeral 126 from a user, such as a medical practitioner. In one embodiment, the external inputs 126 provided by the medical practitioner may include a plurality of learning parameters 128. In another embodiment, the medical practitioner may directly provide the plurality of learning parameters 128 to the user interface unit 112 or to the model generator unit 114. Additionally, or alternatively, at least some of the plurality of learning parameters 128 are provided to the model generator unit 114 by the image acquisition unit 110. The plurality of learning parameters is required to select a deep learning model, decide the architecture of the deep learning model and process the real-time images using the optimized deep learning model. The plurality of learning parameters 128 is used along with the plurality of training images to train a deep learning model. The plurality of learning parameters 128 may include one or more of a type of deep learning model, a number of stages in the deep learning model, and a number of parameters corresponding to each stage of the deep learning model. In an embodiment, when a convolution neural network is used as the deep learning model, the plurality of learning parameters 128 includes number of input feature maps and a number of output feature maps in each stage of the deep learning model. In one embodiment, the input feature maps are two-dimensional input data for a stage in the convolution neural network and the output feature maps are two-dimensional output data for the stage. In other embodiments, higher dimensional input feature maps and higher dimensional output feature maps are used. Further, the plurality of learning parameters includes a plurality of filter classes. In one embodiment, the plurality of filter classes may be specified by the medical practitioner. In other embodiment, the filter classes refer to domain specific filters or pre-determined filters suitable for a specific processing task.

The model generator unit 114 is communicatively coupled to the image acquisition unit 110 and the user interface unit 112. The model generator unit 114 is configured to generate an optimized deep learning model based on the inputs received by the image acquisition unit 110, user interface unit 112, and a memory unit 118. In one embodiment, the deep learning model is a convolution neural network that may have one or more convolution layers. The convolution neural network may be designed to perform a specified task. In one example, the convolution neural network is designed to identify a character in an input image. In another example, the convolution neural network is designed to generate a diagnostic image based on the plurality of real time images 122 generated by the imaging modality, such as the imaging modality 102. In another example the convolution neural network is designed to generate a category of reusable filters corresponding to one or more of the plurality of real time images 122 generated by the imaging modality 102. The model generator unit 114 is configured to determine the plurality of reusable filters in the convolution neural network to determine an optimized convolution neural network.

In one embodiment, the model generator unit is also configured to modify one or more of the plurality of architecture parameters for improving the system performance. For example, in one embodiment, the model generator may determine a different number of optimal seed filters other than provided by the medical practitioner. In another embodiment, the model generator is configured to receive memory space limitation as a constraint parameter and generate optimal layer filters operable within the memory constraint. In such embodiments, the number of optimal filters and the size of the optimal filters are automatically determined by the model generator. In other embodiments, the model generator may automatically determine the optimal filters based on the available training data, nature of the task to be accomplished by the deep learning network with due considerations to other architectural parameters chosen by the medical practitioner.

The processor unit 116 is communicatively coupled to the image acquisition unit 110 and the model generator unit 114 and configured to determine the health condition 108 of the subject based on the inputs received from the image acquisition unit 110 and the model generator unit 114. By way of example, the processor unit 116 is configured to receive the plurality of real time images 122 from the image acquisition unit 110 and the deep learning model 130 from the model generator unit 114. Further, the processor unit 116 is configured to process the plurality of real time images 122 using the deep learning model 130 to determine the health condition 108 of the subject. Moreover, the processing unit 116 is configured to provide the determined health condition 108 to the medical practitioner through an output device such as a display device 132.

The processor unit 116 may include one or more processors. The terms 'processor unit', 'one or more processors,' and 'processor' are used equivalently and interchangeably. The processor unit 116 includes at least one arithmetic logic unit, a microprocessor, a general purpose controller, a graphics processing unit (GPU) or a processor array to perform the desired computations or run the computer program.

While the processor unit 116 is shown as a separate unit in the embodiment of FIG. 1, one or more of the units 110, 112, 114 may include a corresponding processor unit. Alternatively, the optimized deep learning sub-system 106 may be communicatively coupled to one or more processors that are disposed at a remote location, such as a central server or cloud based server via a communications link such as a computer bus, a wired link, a wireless link, or combinations thereof. In one embodiment, the processor unit 116 may be operatively coupled to the image acquisition unit 110, the user interface unit 112 and the model generator unit 114. In yet another embodiment, the processor unit 116 may be configured to perform the functions of the various units of the optimized deep learning sub-system 106.

Moreover, the memory unit 118 may be a non-transitory storage medium. For example, the memory unit 118 may be a dynamic random access memory (DRAM) device, a static random access memory (SRAM) device, flash memory or other memory devices. In one embodiment, the memory unit may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. A non-transitory computer readable medium may be encoded with a program to instruct the one or more processors to determine an optimized deep learning sub-system 106.

Furthermore, at least one of the units 110, 112, 114 may be standalone hardware components. Other hardware implementations such as field programmable gate arrays (FPGA), application specific integrated circuits (ASIC) or customized chip may be employed for one or more of the units of the system.

Figure 2:
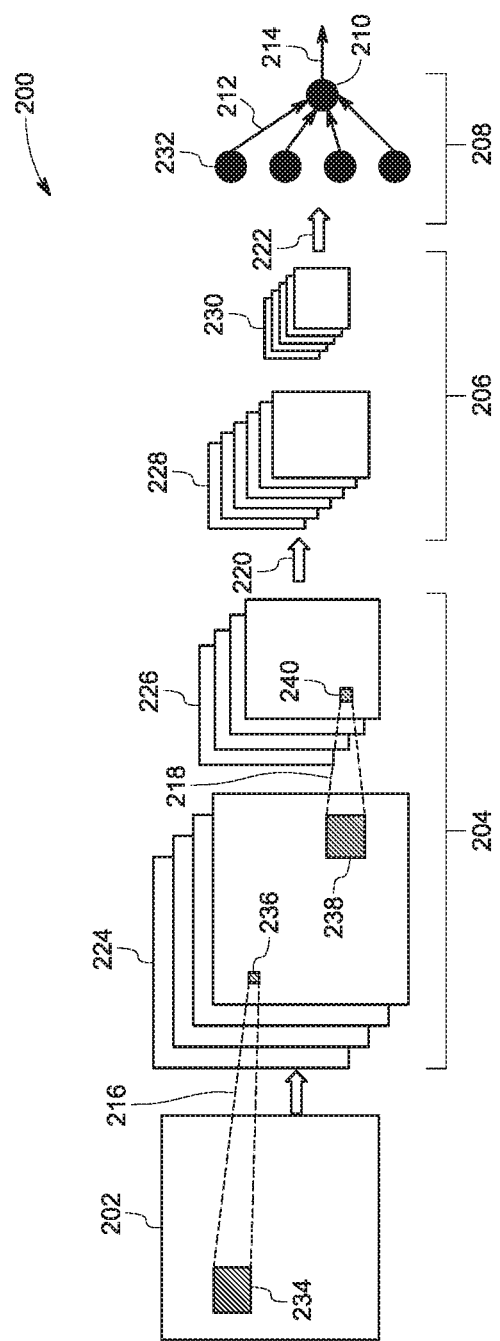
FIG. 2 is a schematic of convolution neural network, in accordance with aspects of the present specification.

FIG. 2 is a schematic of a convolution neural network (CNN) 200, in accordance with aspects of the present specification. In the illustrated embodiment, the convolution neural network 200 receives an input image 202 corresponding to one of the plurality of real time images 122 of FIG. 1. The CNN 200 includes a plurality of convolution stages 204, 206 and a neural network 208. A first convolution stage 204 includes a first plurality of feature maps 224 in cascade with a first plurality of sub sampled images 226. The first plurality of feature maps 224 forms a first convolution filtering layer and the first plurality of sub sampled images 226 form a first sub-sampling layer. The first plurality of feature maps 224 is sub sampled using a sub-sampling operation 218 to generate the first plurality of sub-sampled images 226. A second convolution stage 206 includes a second plurality of feature maps 228 in cascade with a second plurality of sub sampled images 230. The second plurality of feature maps 228 form a second convolution filtering layer and the second plurality of sub sampled images 230 form a second sub sampling layer. The plurality of convolution stages 204, 206 extracts features in stages that are helpful in performing the intended task of the convolution neural network.

The neural network 208 includes a plurality of input nodes 232 and, and at least one output node 210. The plurality of input nodes 232 form an input layer of the neural network 208 and the at least one output node 210 forms an output layer. The neural network 208 may include a plurality of hidden nodes (not shown) in cascade with the plurality of input nodes 232 forming a hidden layer. In some embodiments, the neural network 208 may include more than one hidden layers. In one embodiment, the plurality of input nodes 232 are obtained based on the pixels of the second sub-sampling layer using a serialization operation, represented by reference numeral 222. The output node 210 is determined based on a linear combination of the plurality of input nodes having an associated weight selected from a plurality of weights 212. The CNN 200 generates an output 214 by transforming the value at the output node 210 using a non-linear function. In one embodiment, the non-linear function is a sigmoid function. In other embodiments, other functions such as, but not limited to, a piecewise linear cutoff function may be used to transform the value at the output node 210. The transformed value at the output node 210 represents the information provides the output of the convolution neural network.

In one embodiment, the input image 202 may be a two-dimensional image having M rows of pixels and N columns of pixels. Further, the input image 202 may have R number of channels. For example, the input image 202 may be a two-dimensional image having 128 rows of pixels and 128 columns of pixels. Further, the input image 202 may be a color image having 3 channels corresponding to red, green and blue pixels. The first convolution stage 204 includes a first plurality of filters having m rows of pixels and n columns of pixels and r number of channels. In one example, the first plurality of filters may have 5 pixels in each row, 5 pixels in each column and the parameter r having a value of one, that is a single channel. The first plurality of filters convolved with the input image 202 generates a first plurality of feature maps 224. In the illustrated embodiment of FIG. 2, 4 two-dimensional filters are used in the first plurality of filters and the convolution operation is denoted by reference numeral 216. The convolution operation 216 transforms a plurality of pixels in block 234 of the input image 202 to a pixel 236 in one of the feature map of the plurality of feature maps 224. The size of block 234, size of first plurality of filters may be specified among the plurality of learning parameters. In one example, where the input image 202 includes a two-dimensional image having 128 number of rows of pixels (M) and 128 number of columns of pixels (N), and the first plurality of filters have 5 rows of pixels (m) and 5 columns of pixels (n), the size of each of the plurality of feature maps has 124 pixels in each row and 124 pixels in each column. In one example, the block 238 of the plurality of pixels in feature map 224 (having two pixels in each row and column) is represented by a single pixel 240 in the sub-sampled feature map. In one embodiment, a value of the pixel 240 is selected as a maximum pixel value amongst the pixel values of the plurality of pixels of the block 238. In another embodiment, an average of four pixels in the block 238 may be used as the value of the pixel 240. In other embodiments, other values may be used for the block size, filter size and sampling factor for the sub-sampling.

The second convolution stage 206 includes a second plurality of filters (not shown in FIG. 2) for generating a second plurality of feature maps 228 using a multidimensional convolution filter 220. The first plurality of sub sampled images 226 are used as input images for the second convolution stage 206. A second plurality of sub sampled images 230 is generated by sub-sampling the second plurality of feature maps 228. In one example of the illustrated embodiment of FIG. 2, 6 two-dimensional filters are used in the second plurality of filters. Further, the pixels of the second plurality of sub sampled images 230 may be used in the plurality of input nodes 232 of the neural network 208.

Referring back to FIG. 1, in some embodiments, the first plurality of filters and the second plurality of filters are determined by the model generator unit 114 of FIG. 1. The processing of the input image 202 and generation of the first plurality of feature maps 224, the first plurality of sub sampled images 226, the second plurality of feature maps 228 and the second plurality of sub sampled images 230 are performed by the processor unit 116 of FIG. 1. Embodiments presented herein generate optimized set of filters for the first plurality of filters and the second plurality of filters. In one embodiment, the optimized filters include a plurality of reusable filters. In another embodiment, the optimized filters belong to a plurality of filter classes which may be optionally reusable.

It may be noted that although the illustrated embodiment provides only 2 convolution stages in the optimized convolution neural network, more number of convolution stages may be used in other embodiments. The number and size of the first plurality of filters, the second plurality of filters may be selected based on the choice of the medical practitioner or based on pre-set guidelines provided to the medical practitioner. Further, a different sampling factor may be used to generate the first sub sampled images and the second sub sampled images. The optimized convolution neural network 200 may also receive other types of images or other types of non-image data in other applications. In such scenarios, the optimized deep learning sub-system 106 of FIG. 1 may generate an application specific pattern as output 108.

Figure 3:
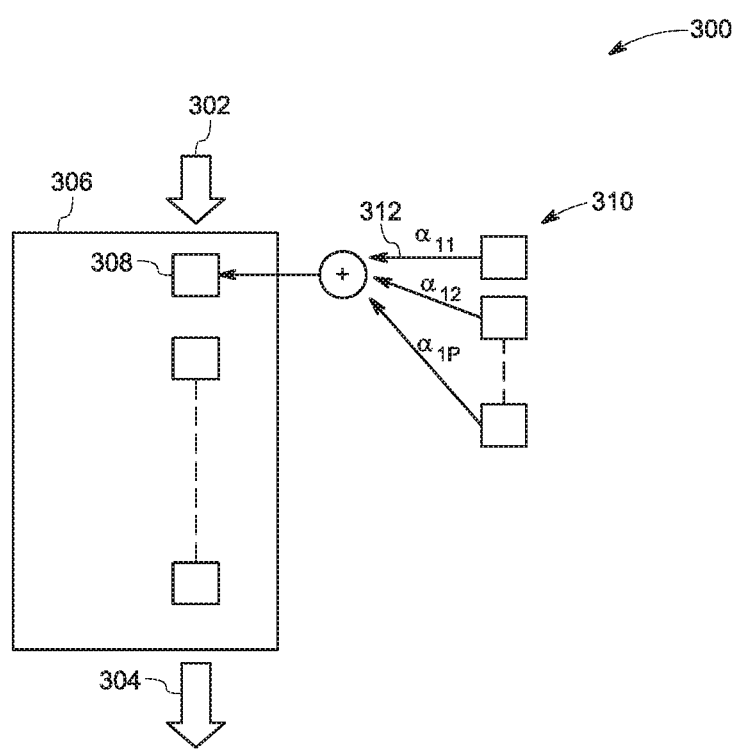
FIG. 3 is a schematic illustrating reuse of filters in the convolution neural network, in accordance with aspects of the present specification.

FIG. 3 is a schematic 300 illustrating reuse of filters in the convolution neural network, in accordance with aspects of the present specification. The schematic 300 illustrates a plurality of input feature maps 302, a plurality of output feature maps 304 and a convolution layer 306 having a plurality of filters 308 of a convolution layer. In one example, the plurality of input feature maps 302 may correspond to the input image 202 and the plurality of output feature maps 304 may correspond to the first plurality of input feature maps 224 of FIG. 2. In another example, the plurality of input feature maps 302 may correspond to the first plurality of input feature maps 224 and the plurality of output feature maps 304 may correspond to the second plurality of input feature maps 228 of FIG. 2. The output feature maps 304 are represented in terms of the input feature maps 302 and the plurality of filters 308 as:

$$G_i = \sigma(\Sigma_k v_{ik} * F_k + b_i) \quad (1)$$

where, $G_i$ is the $i^{th}$ output feature map of the plurality of output feature maps, $v_{ik}$ is a filter among the plurality of filters that provides contribution of input feature map $F_i$ to the output feature map $G_k$. The term $\sigma$ is representative of a non-linearity, and the term $b_i$ is a bias required for regularized solution. In an example, where the dimensionality of input feature maps $\{F_i\}$ is N, and the dimensionality of output feature maps $\{G_i\}$ is M, the dimensionality of the plurality of filters $\{v_{ik}\}$ is MN (the product of M and N).

In one embodiment, the model generator unit 114 of FIG. 1 is configured to determine a plurality of seed filters 310 represented as $\{d_k\}$ having a reduced dimensionality P compared to the dimensionality of the plurality of filters 308 represented as $\{v_{ik}\}$. Specifically, the optimized deep learning model selects the value of P satisfying the condition N<P<<MN. The output feature map 304 is represented by:

$$G_i = \sigma(\Sigma_{k \in P} d_{ik} * F_k + b_i) \quad (2)$$

where, the $\{d_{ik}\}$ represent an optimal N-subset of P filters corresponding to the $i^{th}$ output feature map. In one embodiment, the optimal subset includes one or more of reusable filters.

In another embodiment, the model generator unit 114 of FIG. 1 is configured to determine a plurality of coefficients corresponding to the plurality of seed filters 310. The output feature map 304 is given by:

$$G_i = \sigma(\Sigma_k (\Sigma_p \alpha_{kp}^i d_p) * F_k + b_i) \quad (3)$$

where, $\{\alpha_{kp}\}^i$ is a set of coefficients 312 corresponding to the $i^{th}$ output feature map 304. The set of coefficients corresponding to all the output feature maps 304 is represented by alpha matrix A of dimension PXMN. In some embodiments, the plurality of coefficients may be determined with additional constraints, such as sparsity constraint, rank constraints, convexity constraint on rows or columns of alpha matrix. For example, the model generator may minimize the number of seed filters for each input feature map 302 (enforced using row convexity constraint). In another example, the model generator may minimize the number of feature maps influenced by each seed filter (enforced using column convexity constraint). The number of parameters of the optimized convolution neural network is reduced to MNP+PS compared to MNS number of parameters of the conventional convolution neural network. In one example having ten input feature maps (N=10), 5 output feature maps (M=5), 20 seed filters (P=20), 121 filter coefficients (S=121), the optimum convolution neural network requires about 3420 parameters. For the same example, the conventional convolution neural network requires about 6050 parameters.

The number of parameters of the optimized convolution neural network is reduced further by constructing a dictionary $D_\alpha$ obtained by a matrix decomposition as:

$$A = D_\alpha B \tag{4}$$

where $D_\alpha$ is of size P×Q and B is a matrix of loading coefficients of size Q×MN. The number of parameters for each layer in this case will be PQ+MNQ+PS.

In another embodiment, the model generator unit 114 of FIG. 1 is configured to determine a dictionary of optimal filters. The output feature map 304 is given by:

$$G_i = \sigma(\Sigma_k D\alpha_{ki} * F_k + b_i) \tag{5}$$

where, D is a dictionary of optimal filters of size S rows and $P_{Low}$ columns such that $P_{Low}$ is smaller than P. In another embodiment, directionality of filters is also identified by determining rotational parameter of filter corresponding to the input feature map. In such an embodiment, the output feature map of Eq. (1) is given by:

$$G_i = \sigma(\Sigma_k(\Sigma_p \alpha_{kp}^i R_{\theta kp} d_p) * F_k + b_i) \tag{6}$$

where, $R_{\theta kp}$ is a rotational parameter corresponding to the $k^{th}$ input feature map and the $p^{th}$ seed filter. The directional parameter is representative of direction along which the filter is applied to the input feature map. In another embodiment, $R_{\theta kp}$ may represent a rigid transformation having translation and scaling parameters along with the rotational parameter.

In a generalized embodiment, the output feature maps 304 are represented in terms of one could generalize Eq. (3) to include non-linear combination of mixing of the optimal filters and coefficients, whose form could be as follows $$G_i = \sigma(\Sigma_k(\varphi_{kw}(\{\alpha_{kp}\}, \{d_p\})) * F_k b_i) \tag{7}$$

where $\varphi_w$ (.)($\alpha_k$, d) is a general non-linear function which can be implemented as a neural network, defined by the weights w.

Although a convolution neural network is considered in the illustrated embodiments of FIG. 2, other deep networks with convolution layers, such as auto encoders, may also use architectural parameters corresponding to one or more convolution filtering layers and one or more sub-sampling layers. In some embodiments, the architectural parameters of one of the layers may also be reused in other layers of the same deep network. In some embodiments, one or more of the plurality of seed filters may be reused in other deep learning architectures or in different layers of the same convolution neural network. It may be noted that, the architectures of deep learning networks reusing the plurality of seed filters need not be identical. The optimal filters for the new deep learning architecture may be derived by learning new set of coefficients (of Eq. 3).

Figures 4, 5:
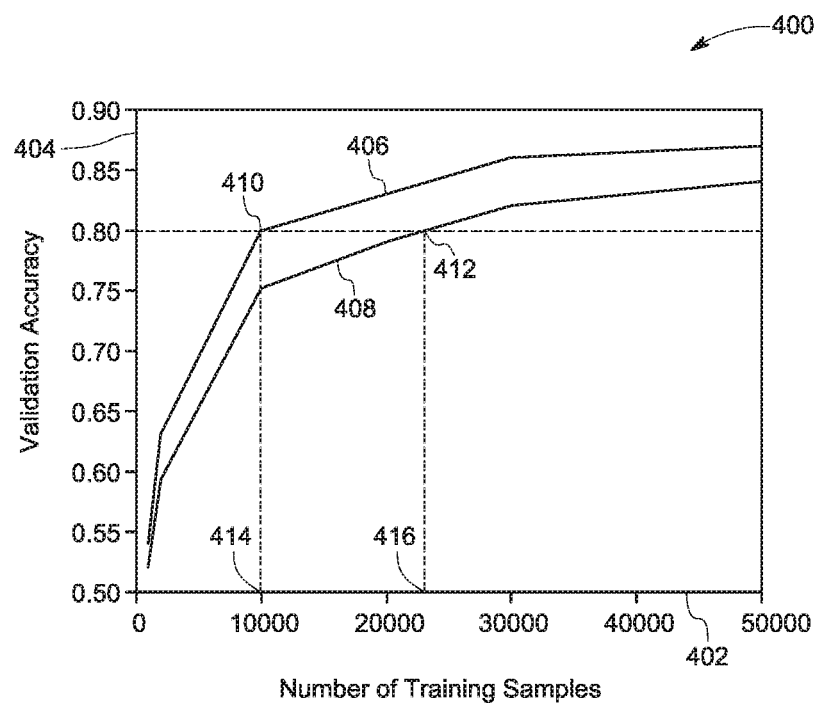
FIG. 4 is a is a graphical representation of performance of optimized convolution neural network, in accordance with aspects of the present specification.
FIG. 5 is a table illustrating computational complexity of optimized convolution neural network, in accordance with aspects of the present specification.

FIG. 4 is a graphical representation 400 of performance of optimized convolution neural network, in accordance with aspects of the present specification. The graph includes an x-axis 402 representative of a number of training images and a y-axis 404 representative of validation accuracy on a scale of zero to one with increasing accuracy from zero towards one. The graph 400 includes a first curve 406 representative of validation accuracy from use of optimized convolution neural network and a second curve 408 representative of validation accuracy from use of conventional deep learning model. The validation accuracy may be determined with reference to a reference model. It may be observed that the curve 406 reaches 80% accuracy at a point 410 corresponding to 10,000 training images represented by point 414. The curve 408 reaches 80% accuracy at a point 412 corresponding to 25,000 training images represented by point 416. The convolution neural network disclosed herein can be optimized with less number of training images compared to the conventional deep learning model.

FIG. 5 is a table 500 illustrating computational complexity of optimized convolution neural network, in accordance with aspects of the present specification. The table 500 provides a comparison of computation complexity of disclosed technique in a handwritten digit classification problem using a two layer CNN. The first layer has 1 input feature map (i.e., the input image) and 10 output feature maps with the 5 seed filters. The second layer has 10 input feature maps and twenty output feature maps with twenty seed filters. About two thousand images are used for training and about ten thousand images are used for validation and testing of the deep learning models designed for handwritten digit classification. The table 500 includes a first row 502 having entries corresponding to filters without sharing and a second row 504 having entries corresponding to filters with sharing. The table includes a first column 506 having entries corresponding to optimized CNN and a second column 508 having entries corresponding to conventional CNN. It may be observed that optimized convolution neural network is capable of providing higher model accuracy (about 94%) compared to conventional CNN (having 85%). Further, the number of parameters corresponding to the optimized CNN is much smaller (about 5000 parameters) compared to requirement of a large number of parameters (more than ten thousand parameters) for conventional CNN. The optimized CNN requires less number of parameters for modelling compared to the convention CNN models.

Figure 6:
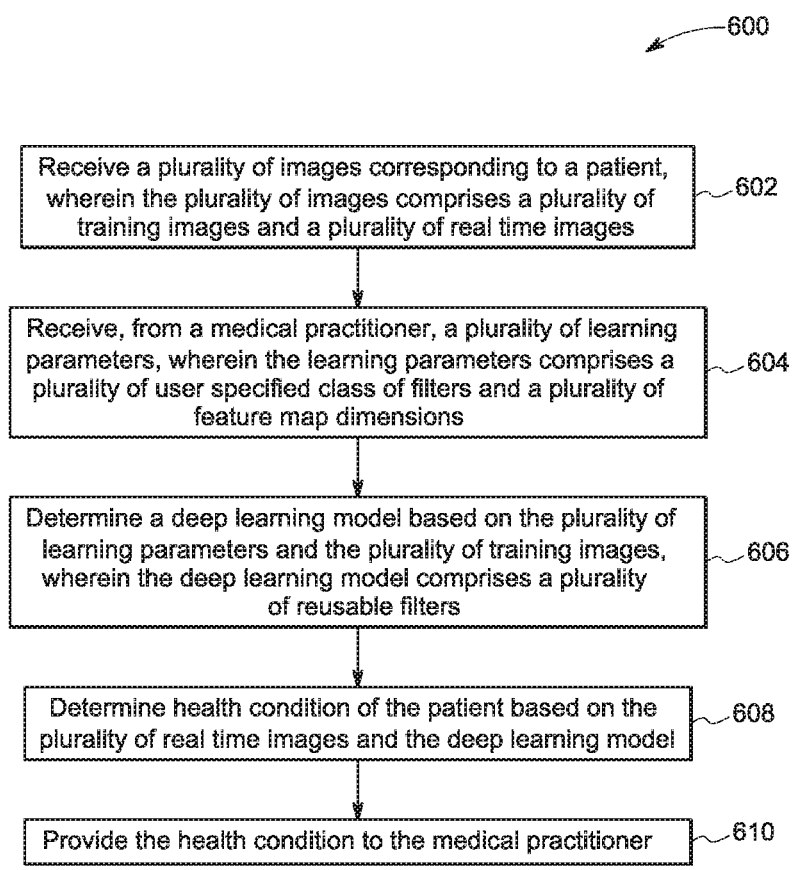
FIG. 6 is a flow chart of a method of optimizing the deep learning architecture, in accordance with aspects of the present specification.

FIG. 6 is a flow chart 600 of a method for optimizing the deep learning architecture, in accordance with aspects of the present specification. At step 602, the method includes receiving a plurality of images corresponding to a subject. The plurality of images comprises a plurality of training images and a plurality of real time images. At step 604, the method further includes receiving a plurality of learning parameters. The plurality of learning parameters includes a plurality of filter classes and a plurality of architecture parameters. At step 606, the method includes determining a deep learning model based on the plurality of learning parameters and the plurality of training images. The deep learning model may be determined by determining a convolution neural network. In one embodiment, the deep learning model comprises a plurality of reusable filters. In one embodiment, determining the deep learning model includes determining a plurality of seed filters. The dimensionality of the seed filters is based on a size of the plurality of training images. In one embodiment, determining the deep learning model comprises determining a plurality of optimal filters among the plurality of seed filters for generating an output feature map of the plurality of output feature maps. In another embodiment, determining the deep learning model comprises determining a coefficient set corresponding to each output feature map of the plurality of output feature maps based on the plurality of seed filters. In one embodiment, determining the deep learning model comprises determining a dictionary of optimal filters for generating the plurality of output feature maps based on the plurality of seed filters.

At step 608, the method further includes determining a health condition of the subject based on the plurality of real time images and the deep learning model. In another embodiment, determining the deep learning model comprises determining a coefficient set corresponding to each output feature map of the plurality of output feature maps based on the dictionary of optimal filters. In one embodiment, determining the health condition includes receiving a plurality of input feature maps. Each of the plurality of input feature maps is a representative of the plurality of images. In another embodiment, determining the deep learning model comprises determining a rotational parameter corresponding to a seed filter among the plurality of seed filters. In a related embodiment, determining the deep learning model includes determining a rigid transformation corresponding to the seed filter. The rigid transformation provides translation, scaling along with the rotation for the seed filter. Further, determining the health condition includes generating a plurality of output feature maps based on the convolution neural network. Each of the plurality of output feature maps is a linear combination of filtered version of the plurality of input feature maps. Each of the plurality of output feature maps is a representation of the input feature maps. Further in step 610, the determined health condition of the subject is provided to the health practitioner for diagnosis and determining treatment options.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method for determining optimized deep learning architecture, comprising:
receiving a plurality of training images and a plurality of real time images corresponding to a subject;
receiving, by a medical practitioner, a plurality of learning parameters comprising a plurality of filter classes and a plurality of architecture parameters;
determining a deep learning model based on the plurality of learning parameters and the plurality of training images, wherein the deep learning model comprises a plurality of filters, wherein the determining the deep learning model comprises reducing a number of the plurality of learning parameters of the deep learning model based at least on one or more constraints that determine a coefficient set that is applied to the plurality of filters, and wherein the coefficient set is determined based on at least a sparsity constraint and a convexity constraint applied to rows or columns of a parameter matrix;
determining a health condition of the subject based on the plurality of real time images and the deep learning model; and
providing the health condition of the subject to the medical practitioner.

2. The method of claim 1, wherein determining the deep learning model comprises determining a convolution neural network, and wherein the plurality of filters comprise at least one reusable filter.

3. The method of claim 2, wherein determining the health condition comprises:
receiving a plurality of input feature maps, wherein each input feature map of the plurality of input feature map is a representation of the plurality of real time images; and
generating a plurality of output feature maps based on the convolution neural network, wherein each of the plurality of output feature map is a linear combination of filtered version of the plurality of input feature maps, wherein each of the plurality of output feature map is a representation of the input feature maps.

4. The method of claim 3, wherein determining the deep learning model comprises determining a plurality of seed filters, wherein dimensionality of the seed filters is based on a size of the plurality of training images.

5. The method of claim 4, wherein determining the deep learning model comprises selecting a plurality of optimal filters among the plurality of seed filters for generating an output feature map of the plurality of output feature maps.

6. The method of claim 4, wherein determining the deep learning model comprises determining the coefficient set corresponding to each output feature map of the plurality of output feature maps based on the plurality of seed filters.

7. The method of claim 4, wherein determining the deep learning model comprises determining a dictionary of optimal filters for generating the plurality of output feature maps based on the plurality of seed filters.

8. The method of claim 7, wherein determining the deep learning model comprises determining the coefficient set corresponding to each output feature map of the plurality of output feature maps based on the dictionary of optimal filters.

9. The method of claim 4, wherein determining the deep learning model comprises determining a rotational parameter corresponding to a seed filter of the plurality of seed filters.

10. A system for determining optimized deep learning architecture, comprising:
a processor unit to:
receive a plurality of training images and a plurality of real time images corresponding to a subject;

receive a plurality of learning parameters comprising a plurality of filter classes and a plurality of architecture parameters;

determine a deep learning model based on the plurality of learning parameters and the plurality of training images, wherein the deep learning model comprises a plurality of filters, wherein the determining the deep learning model comprises reducing a number of the plurality of learning parameters of the deep learning model based at least on one or more constraints that determine a coefficient set that is applied to the plurality of filters, and wherein the coefficient set is determined based on at least a sparsity constraint and a convexity constraint applied to rows or columns of a parameter matrix;

determine a health condition of the subject based on the plurality of real time images using the deep learning model; and provide the health condition of the subject to a medical practitioner.

11. The system of claim 10, wherein the deep learning model comprises a convolution neural network, and wherein the plurality of filters comprise at least one reusable filter.

12. The system of claim 11, wherein the processor unit is configured to:

receive a plurality of input feature maps, wherein each input feature map of the plurality of input feature map is a representation of the plurality of real time images; and generate a plurality of output feature maps based on the convolution neural network, wherein each of the plurality of output feature map is a linear combination of filtered version of the plurality of input feature maps, wherein each of the plurality of output feature map is a representation of the input feature maps.

13. The system of claim 12, wherein the convolution neural network comprises a plurality of seed filters, wherein dimensionality of the seed filters is based on a size of the plurality of training images.

14. The system of claim 13, wherein the processor unit is configured to select a plurality of optimal filters among the plurality of seed filters for generating an output feature map of the plurality of output feature maps.

15. The system of claim 13, wherein the processor unit is configured to determine the coefficient set corresponding to each output feature map of the plurality of output feature maps based on the plurality of seed filters.

16. The system of claim 13, wherein the processor unit is configured to determine a dictionary of optimal filters for generating the plurality of output feature maps based on the plurality of seed filters.

17. The system of claim 16, wherein the processor unit is further configured to determine the coefficient set corresponding to each output feature map of the plurality of output feature maps based on the dictionary of optimal filters.

18. The system of claim 13, wherein the processor unit is further configured to determine a rotational parameter corresponding to a seed filter among the plurality of seed filters.

19. A health diagnostic system comprising:
an imaging modality;
a sub-system comprising:
a processor unit to:
receive a plurality of training images and a plurality of real time images corresponding to a subject;
receive a plurality of learning parameters comprising a plurality of filter classes and a plurality of architecture parameters;
determine a deep learning model based on the plurality of learning parameters and the plurality of training images, wherein the deep learning model comprises a plurality of filters, wherein at least one of the plurality of filters is a reusable filter, wherein the determining the deep learning model comprises determining a coefficient set that is applied to the plurality of filters, wherein the coefficient set is determined based on at least a sparsity constraint and a convexity constraint applied to rows or columns of a parameter matrix;
determine a health condition of the subject based on the plurality of real time images using the deep learning model; and
provide the health condition of the subject to a medical practitioner.

20. The health diagnostic system of claim 19, wherein the deep learning model comprises a convolution neural network, and wherein the processor unit is configured to determine the coefficient set based on a combination of the sparsity constraint, the convexity constraint, and a rank constraint.

* * * * *